(12) United States Patent
Fletcher (10) Patent No.: US 8,240,314 B2
(45) Date of Patent: Aug. 14, 2012

(54) METHOD FOR INJECTING FILLERS INTO THE DERMIS

(75) Inventor: Leslie C. Fletcher, Torrance, CA (US)

(73) Assignee: Eden Esthetics, A Professional Nursing Corporation, Torrance, CA (US)

( * ) Notice: Subject to any disclaimer, the term of this patent is extended or adjusted under 35 U.S.C. 154(b) by 255 days.

(21) Appl. No.: 12/798,577

(22) Filed: Apr. 6, 2010

(65) Prior Publication Data

US 2010/0256553 A1  Oct. 7, 2010

Related U.S. Application Data

(60) Provisional application No. 61/212,063, filed on Apr. 6, 2009.

(51) Int. Cl.
 *A61B 19/00* (2006.01)
(52) U.S. Cl. ........................................................ 128/898
(58) Field of Classification Search .................... 604/28; 128/898
 See application file for complete search history.

(56) References Cited

OTHER PUBLICATIONS http://arquederma.com/, accessed Feb. 11, 2012.*
Leslie Fletcher, Injectable Thread Lift, MedEsthetics Magazine, pp. 12,14,63, Jan./Feb. 2009.*
http://edenestheticnursing.wordpress.com/, dated Sep. 20, 2008, accessible at http://web.archive.org/web/20110207221544/http://edenestheticnursing.com/, "Come learn about Leslie's new injectable threadlift technique", 3 pages.*
http://edenestheticnursing.wordpress.com/, dated Sep. 20, 2008, accessible at http://web.archive.org/web/20110207221544/http://edenestheticnursing.com/, "About Leslie", 1 page.*
van Eijk, Tom; Martin Braun,. "A novel method to inject hyaluronic acid: the Fern Pattern Technique." Journal of Drugs in Dermatology. 2007. Retrieved Oct. 7, 2010 from accessmylibrary: http://www.accessmylibrary.com/coms2/summary_0286-32771272_ITM.

* cited by examiner

*Primary Examiner* — William H. Matthews
(74) *Attorney, Agent, or Firm* — Tope-McKay & Associates; Marcus Risso (57) ABSTRACT

Described is a method for injecting fillers into the dermis. The method provides a technique for arcing the needle to create a lasting support structure within a patient's dermal tissue. Described is an act of inserting a needle attached to a syringe filled with a dermal filler into a patient's facial dermis at a strategic insertion point. Once inserted, pressure is applied to hub of the needle to cause it to arc within the dermis and create pockets of space within the dermis. The needle is used to dissect the tissue in the subepidermal plane that is creating the depression showing on the epidermis. The syringe is used to release the filler into the dermis while simultaneously applying pressure to the hub of the needle while withdrawing the needle from the patient's dermis. Filler is injected strategically within the patient's dermis to raise a facial depression, wrinkle, or fold.

5 Claims, 7 Drawing Sheets

METHOD FOR INJECTING FILLERS INTO THE DERMIS

PRIORITY CLAIM

This is a Non-Provisional Utility Patent Application of U.S. Provisional Application No. 61/212,063, filed on Apr. 6, 2009, entitled, "METHOD FOR INJECTING FILLERS INTO THE DERMIS."

BACKGROUND OF THE INVENTION (1) Field of Invention

The present invention relates to a method for lifting the dermis of a patient's face and more particularly, to an arcing technique for injecting fillers into the dermis of a patient.

(2) Description of Related Art

Facial lifts or treatments are a relatively recent phenomenon. Such techniques or treatments are often used in cosmetic procedures to decrease wrinkles and the appearance of aging. As can be appreciated, a variety of techniques have been marketed and implemented to treat the appearance of aging.

For example, fillers are often used to add volume to a patient's face. More specifically, facial fillers are commonly injected into the nasolabial folds (NLFs) in the face, which increasingly deepen upon aging. To prevent the deepening of the NLF, the technique fills the NLF with a volumizer to correct the loss of midface volume.

There are many techniques for injecting dermal fillers; serial puncture, linear threading, crosshatching, and fanning, to name a few. While these techniques are useful in their own right, they tend to be less permanent as the filler is absorbed by the body and needs replacement. Further, such techniques do nothing to provide a lasting support or column structure underneath the skin to support the skin.

Thus, a continuing need exists for a technique for lifting a patient's face that provides a lasting and supportive effect.

SUMMARY OF INVENTION

While considering the failure of others to make use of all of the above steps or techniques in this industry, the inventor unexpectedly realized that providing support columns through the collapsing skin through an arcing filler technique, would provide a lasting and supportive lifting effect to the patient's face and, as such, decrease wrinkles and the appearance of aging.

Thus, the present invention is a method for injecting a filler into the dermis using an arcing technique to provide such a lasting and supportive lifting effect. The method includes an act of inserting a needle attached to a syringe filled with a filler into a patient's facial dermis at a strategic insertion point. Once inserted, pressure is applied to hub of the needle to cause it to arc within the dermis and create pockets of space within the dermis. The needle is used to dissect the tissue in the subepidermal plane that is creating the depression, or groove, showing on the epidermis. The syringe is used to release the filler into the dermis while simultaneously applying pressure to the hub of the needle while withdrawing the needle from the patient's dermis. Filler is injected strategically within the patient's dermis to raise a facial depression, wrinkle, or fold.

In another aspect, the insertion point is approximately one centimeter lateral and one centimeter superior to a fold that is associated with the facial depression.

Additionally, the needle is injected into the dermis until it is approximately one half a centimeter past the fold.

In releasing filler into the dermis, pressure is applied to the needle and the needle is withdrawn such that as the needle exits the patient, the needle is at an angle with respect to the patient in a range of 60 to 75 degrees.

Further, in applying pressure to the needle hub to cause it to arc within the dermis and create pockets in the dermis, the fibroblasts within the dermis are intentionally stretched through creating pockets in the dermis, thereby stimulating the fibroblasts to synthesize type 1 collagen and support the facial depression.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a method for lifting the dermis of a patient's face and more particularly, to an arcing technique for injecting fillers into the dermis of a patient. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Introduction

The present invention relates to a method for injecting fillers into the dermis to reassign volume into the "triangle of beauty", while supporting the falling skin, with created structural columns. The triangle of beauty is an area of the face that is framed by the cheekbone and chin which tend to sag and become square as people age. The procedure according to the present invention tacks the skin back into the triangle of beauty, negating, or prolonging the need for surgery.

While there are many techniques to injecting dermal fillers (e.g., serial puncture, linear threading, crosshatching, and fanning), the present invention improves upon the prior art through an "arcing" technique that strategically places columns to redirect the skin upward.

It is important to realize that the skin is a three-dimensional structure. The current injection techniques treat the skin in only two dimensions (i.e., in the prior art, the filler is placed all in the same depth in the dermis). With the arcing method of the present invention, filler is injected along a path of variable depths using one continuous thread, creating an arc of support for the overhangs. Because of this variation, the arcing method offers another major advantage of the prior art; Scaffolding is created which prevents folding of the skin in this area, keeping the crease from being created during animation.

Figure 1:
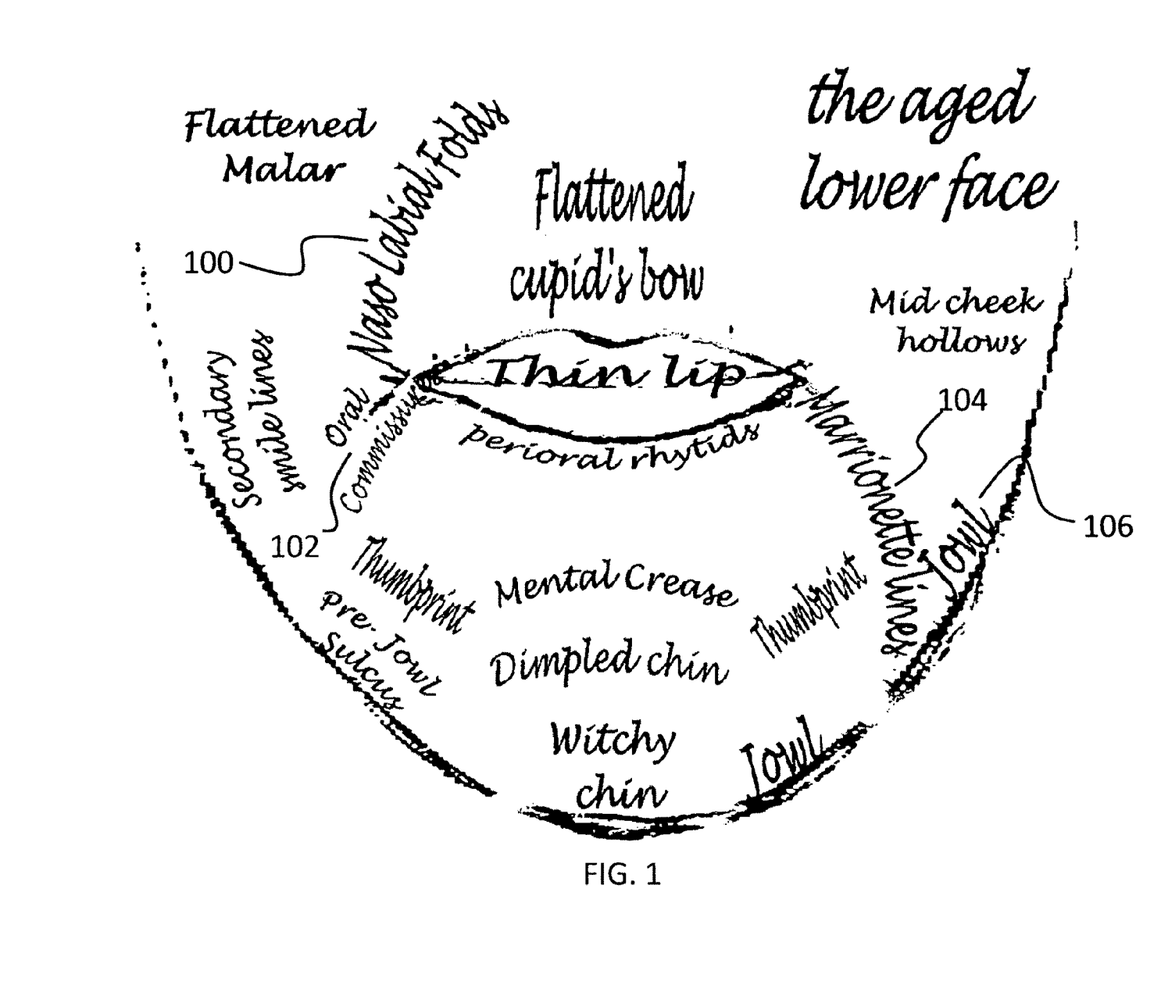
FIG. 1 is an illustration of an aged, lower face, depicting the various wrinkle lines of a patient.

The areas that respond best are the areas that are most in need of "volume reassignment" or otherwise areas of skin on the face that needs to be redirected. First and as shown in FIG. 1, would be the nasolabial fold 100, or nasolabial groove. Then there are the oral commisures 102, the marionettes 104, and the jowls 106. All of these "overhangs" describe too much volume in all the wrong places. They are usually created by volume that used to be somewhere else; volume that has descended downward and landed in the fold, or overhang. These areas can be masked by "packing" product next to the mound (as performed in the method of the prior art), or the mound can be lifted up and put back where it used to be. How can this be accomplished? Surgery is of course always an option. But not all patients have that choice; due to lack of funds, or downtime. In light of this, the present invention provides a technique that gives a very similar effect to that of a surgical thread lift, but without the surgery.

(2) Specific Details

Figure 2:
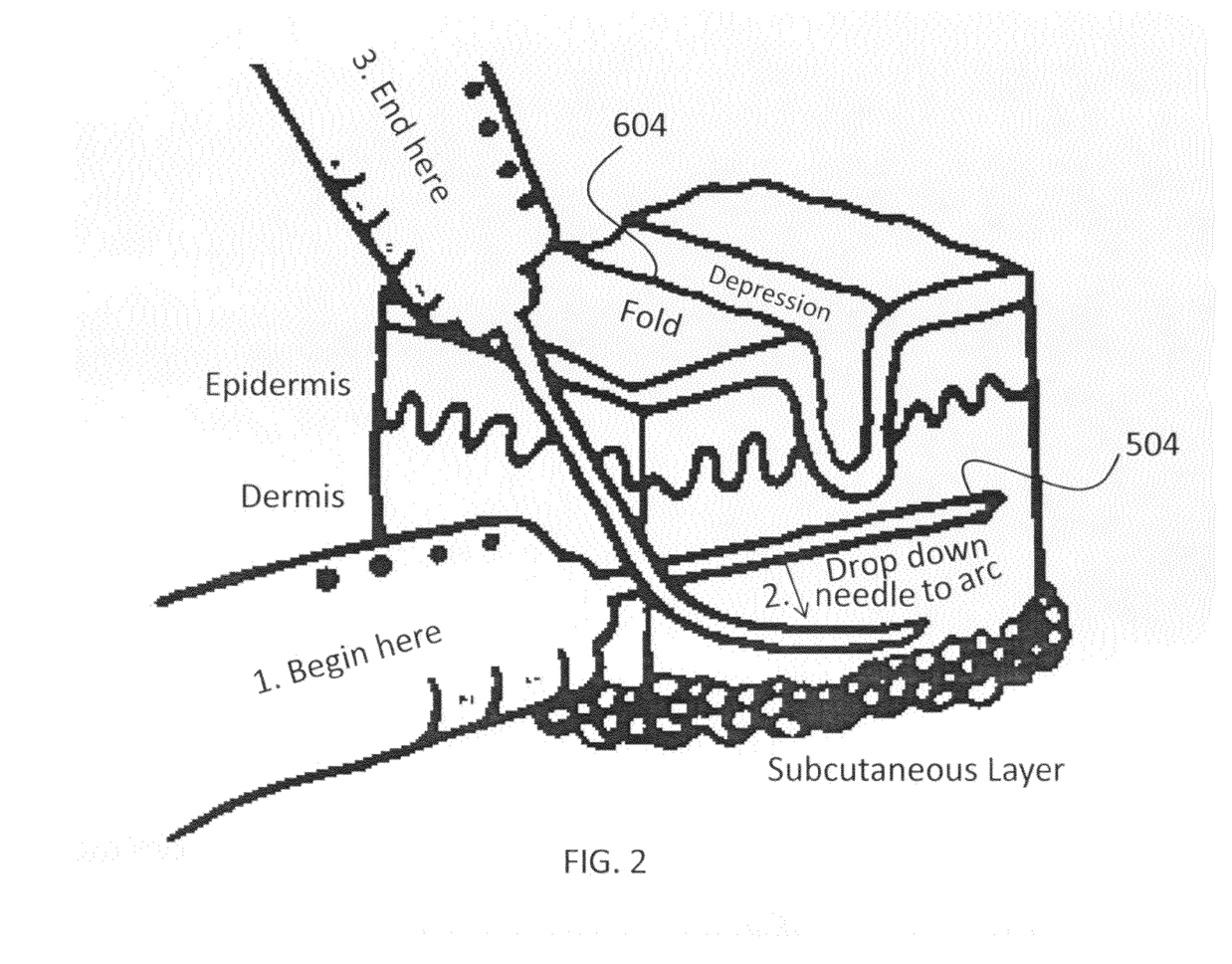
FIG. 2 is an illustration depicting insertion of a needle into a patient and arcing the needle.

As noted above, the present invention is a method for injecting fillers into the dermis. The method improves upon the prior art by putting support columns through the collapsing skin. This is accomplished through an "arcing" technique of lifting in upward vectors while injecting. As shown in FIG. 2, while injecting superior to inferior in a retrograde threading technique, the needle is flexed to shape it into an arc.

Figure 3:
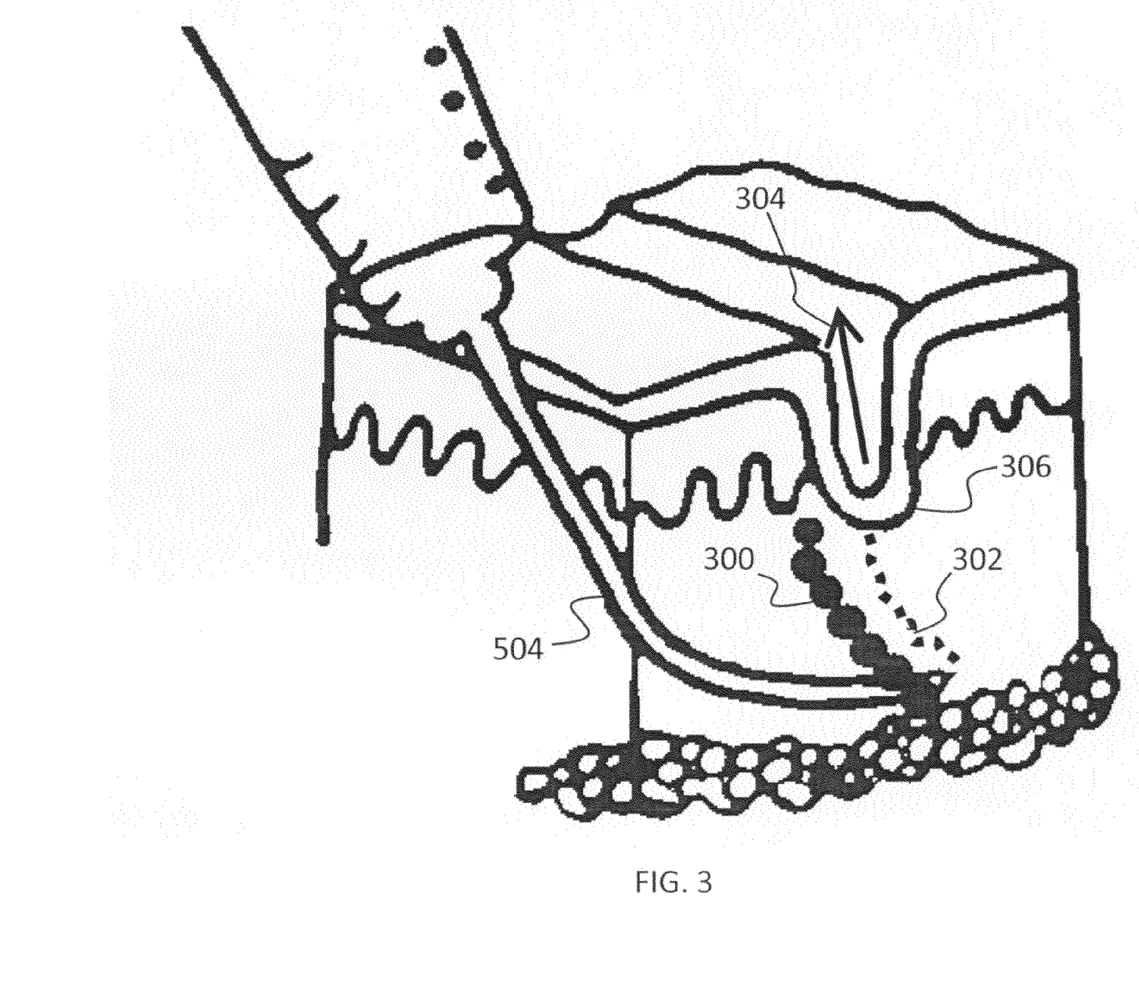
FIG. 3 is an illustration depicting "pocketing" and filling according to the present invention.

The arcing of the needle often results in a crunching noise, followed by a beautiful "fill" of the product, as shown in FIG. 3. The fill is referred to as "pocketing". Technically, it is the release of dermal attachments and the creation of space for the placed filler, followed by desired scar tissue as the filler goes in an upward vector. This phenomenon leads to neocollagenesis, which in turn, leads to an increase in longevity of the product being used.

As a technique that provides the filler three-dimensionally, filler is placed along a path of variable skin depths to create an arch of support for the crease. Because of this variation, the scaffolding is created which prevents folding of the skin in this area, keeping the crease from being created during facial muscle activity. This is noted both at rest and during animation.

In performing the present invention, the procedure should be treated like any other injectable filler treatment, in which the patient is advised of the risk and benefits, in conjunction with a review of their medications and medical history. Once performed, it is desirable to follow up with the patient later to ensure that the injections are symmetrical, and to check for any complications.

Figure 4A:
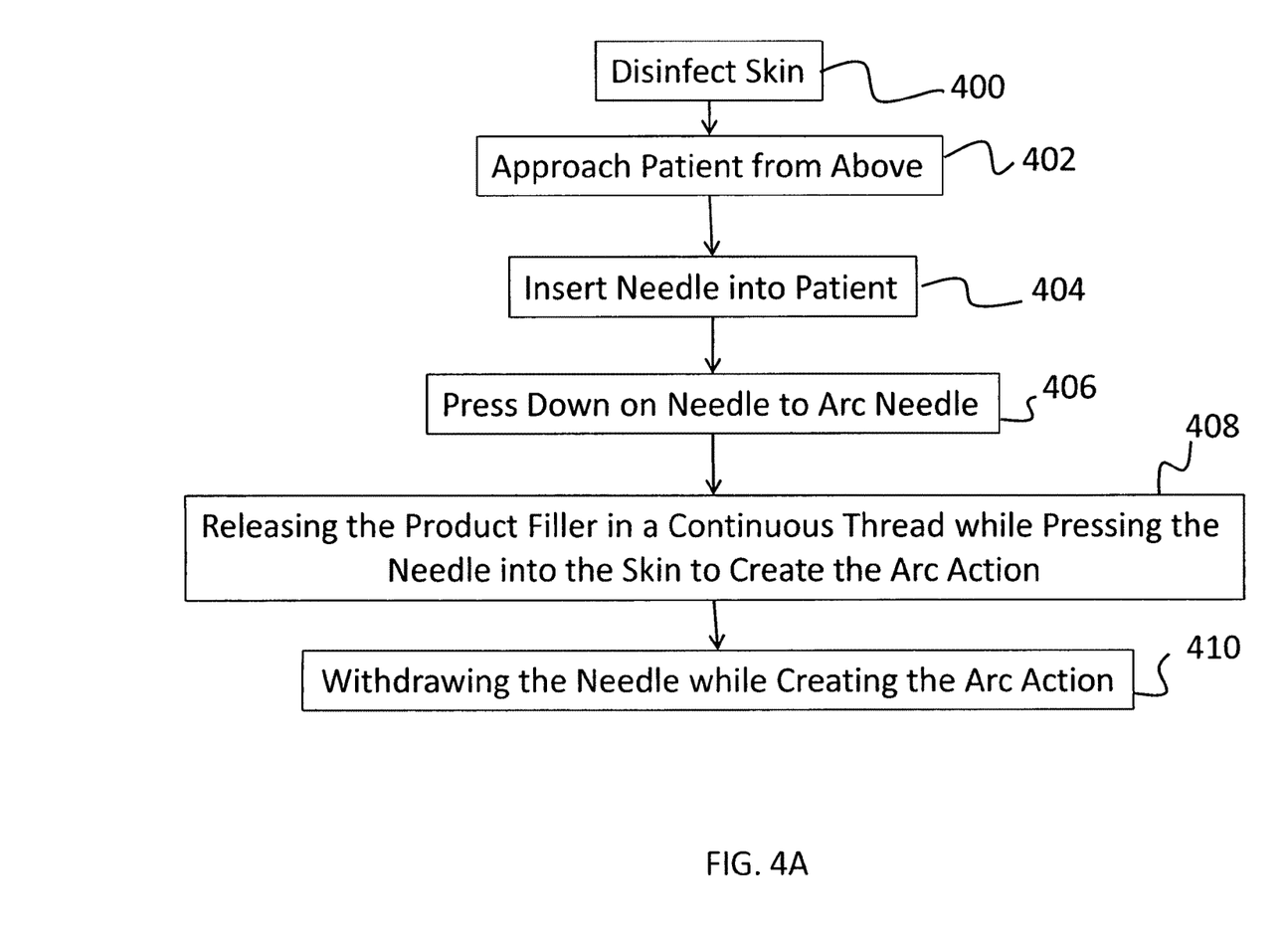
FIG. 4A is a flow chart illustrating the technique according to the present invention.

A detailed step-by-step description of the technique is as follows and depicted in FIG. 4A. A topical numbing cream can optionally be applied to numb the area to be treated. Then the skin is to be cleaned and disinfected 400 using an antiseptic or disinfectant. As a non-limiting example, alcohol is applied to the skin, with it thereafter evaporating prior to injection of the filler. Further, it should be established where the columns are to be created using an applicator (e.g., cotton-tipped applicator) to determine maximal lifting benefit. A marking utensil (such as a clean, white pencil) is used to draw on the patient the approximate position of the columns, which are desirably approximately one to two centimeters apart. A nerve block can also be performed at this time if necessary.

Figure 5:
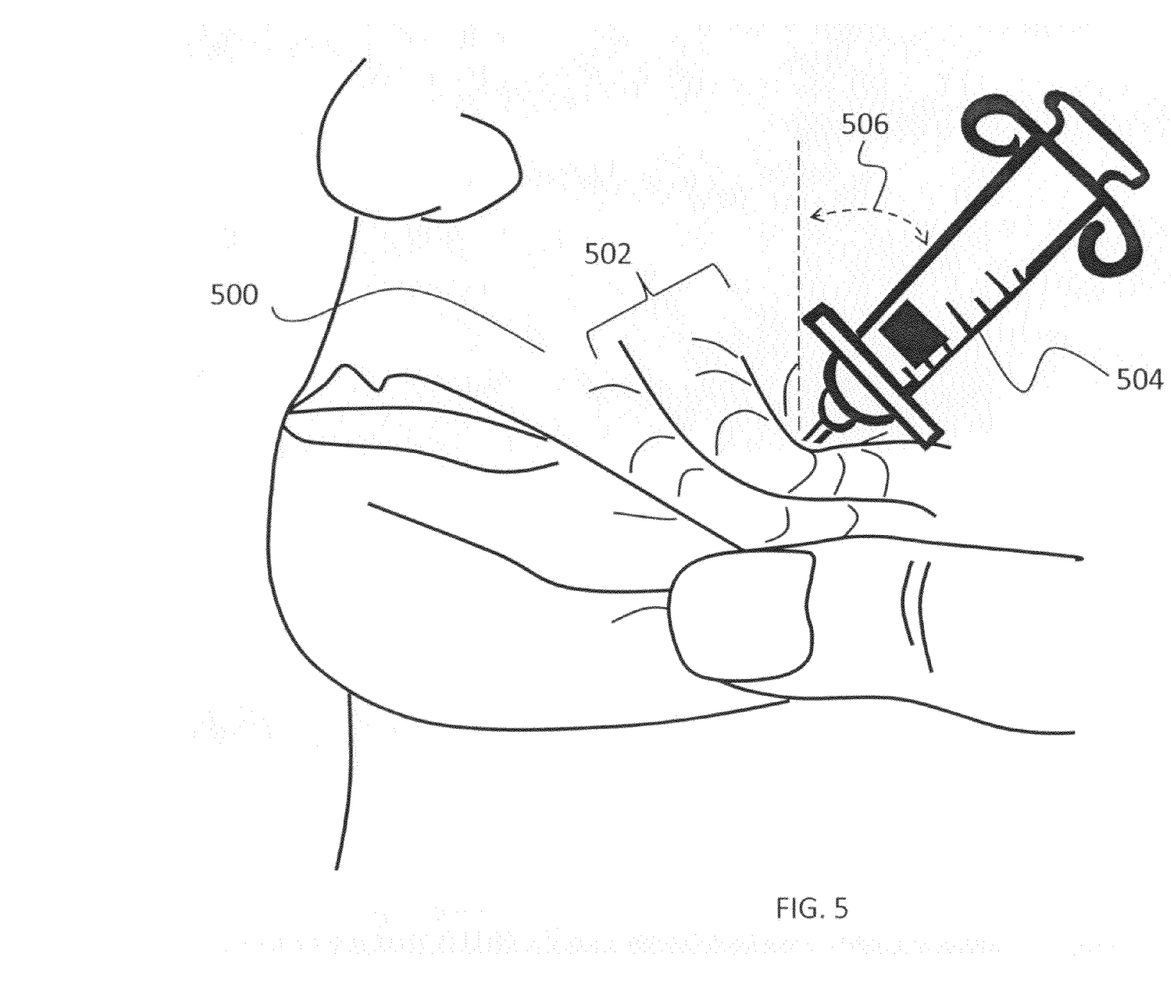
FIG. 5 is an illustration depicting an "accordion style" technique in which the patient's skin is bunched up.

Prior to initiating the injections, it is recommended that the appropriate length of needle be selected for the area of face that is to be treated. For example, a longer needle (e.g., 1 to 1 and ¼ inches) works well on some faces, because there is more surface area to pull away from, giving more of the appearance of a mid face thread lift by involving the lateral malar eminence. However, with the long needle, the person performing the injection needs to remember to use a thick enough thread to make it supportive. A smaller needle (e.g., ½ to ¾ of an inch) works great as well because it is easier to control than the longer needle and provides a thicker rod for support. When using a smaller needle, an "accordion style" technique can be used to make the shorter length work longer. In other words, when reaching the hub of the needle, the user can continue pushing. As depicted in FIG. 5, the patient's skin 500 can be bunched up 502 in order to gain more distance with the short needle 504.

Next and referring again to FIG. 4A, once the appropriate needle is selected the patient is approached 402 from above their face. In other words, the patient should be approached 402 from the top or superior end of the patient (which is depicted as element 600 in FIG. 6). As can be appreciated by one skilled in the art, although the technique can be performed while approaching the patient from their bottom end (i.e., below the patient), the present invention is desirably performed while approaching 402 the patient from the top or superior end (i.e., from above the patient) which allows for the upward pull, or vector that is applied in an upward pull, direction, or vector.

Figure 6:
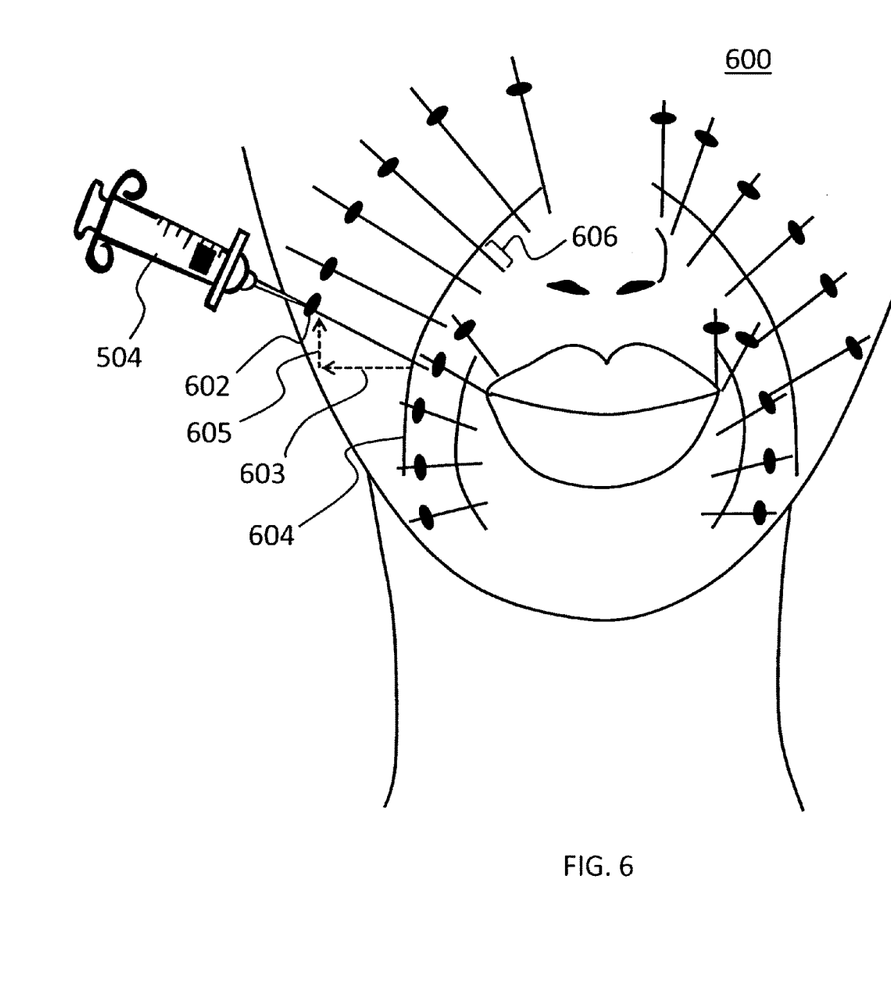
FIG. 6 is an illustration depicting various insertion points and thread lines in a patient's face that span across depressions or wrinkles.

After taking the appropriate position, the needle is inserted 404 into the patient. Desirably, the needle is inserted 404 perpendicular to the target area (e.g., fold, groove, overhang, or wrinkle). As depicted in FIG. 6, the insertion point 602 of the needle 504 should be approximately one centimeter lateral 603 and one centimeter superior 605 to the fold 604 (also depicted in FIG. 2). As can be appreciated by one skilled in the art, the dimensions described herein are approximate and can be varied per the patient and clinician (i.e., user of the present invention) performing the technique. Desirably, the needle 504 should be inserted into the patient such that it proceeds past 606 the fold 604 by about one half a centimeter. Again, the patient is approached from above 600 to provide the most effective lift.

Referring again to FIG. 4A, the needle is inserted 404 in a similar manner as any other type of retrograde thread injection. The needle is inserted into the appropriate depth for the corresponding filler, erring slightly on the more superficial side. For example, Radiesse® would be in the deep reticular/subcutaneous junction, while Hyaluronic acids would be in the mid to upper reticular dermis. This is because the clinician performing the technique will end up bearing down on the needle a bit while injecting and placing the material a little deeper than the initial needle placement.

Once the desired depth is reached, the needle is pressed 406 to bear down into the skin slightly. FIG. 2 depicts this act further, in which the needle 504 is inserted into the dermis and pressed down. This will cause the needle 504 to "flex" or "arc." Referring again to FIG. 4A, as the needle is pulled out, the user continues to push the needle down against the skin and arc upward, tugging as they ascend to the end of the needle, finishing with the end of the syringe at a 60-75 degree angle. Although FIG. 5 is used to depict the "accordion style" injection, it also depicts an angle 506 between the needle and the patient such that as the needle exits the patient, the needle is at the angle 506 with respect to the patient in the above listed range of 60 to 75 degrees.

In withdrawing the needle, the user continues to arc the needle and push on the plunger, slowly releasing the product in a continuous thread. A little more of the filler should be placed on the other side of the fold and tapered off as the needle ascends, remembering to stop short of the tip or insertion point. This helps to tether the skin as it is redirected it upwards. The words that come to mind to describe this idea, while far from medical, are effective: such as "scooping" and "gathering" as if to redirect the loose skin and "staple" it into place. Thus, the invention includes an act of releasing the product 408 in a continuous thread while pressing the needle into the skin to create the arc action, while simultaneously withdrawing 410 the needle. In performing this action, the user should feel, and hear, some crunching, and releasing of the dermal attachment. It should feel as if when the user is laying down the "thread" of product, the user is pulling the skin, and stapling it in the desired direction, mainly in an upward vector. Desirably, the needle should not be bent when it exits the skin. The user should press hard enough to flex the needle, but not too hard as to bend it. At this time and as shown in FIG. 3, the user will see the product 300 fill beautifully in the pockets 302 that have just been created with the needle 504, which raises 304 the skin from the depression 306 to decrease the wrinkle or appearance of aging.

Figure 4B:
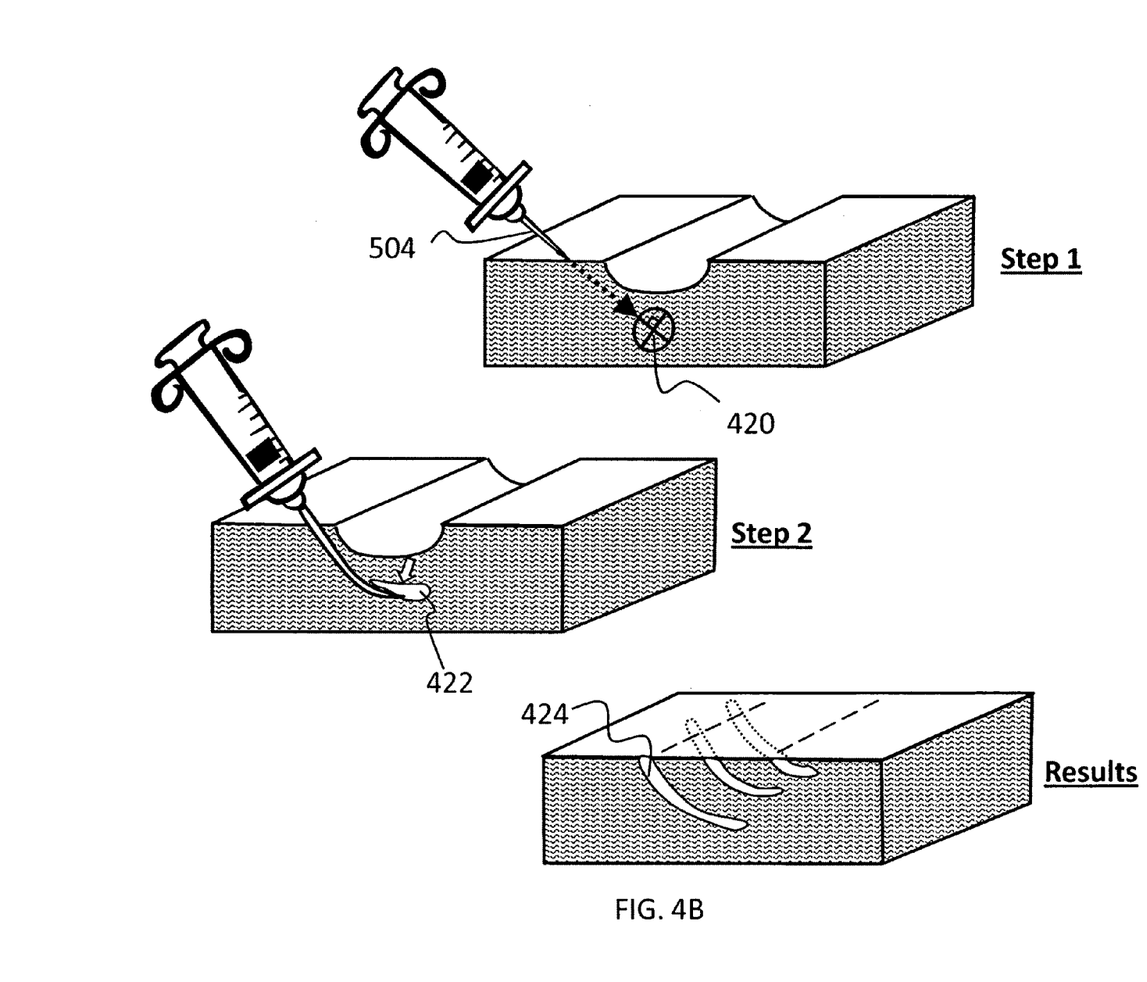
FIG. 4B is an illustration depicting the technique according to the present invention.

The process described above is further depicted in FIG. 4B, which illustrates two steps and the end result. As shown, the needle 504 is inserted into the patient at an angle such that it is approximately perpendicular to the target point 420 (which typically includes intact fibers). As the needle 504 is inserted (or once already inserted), the clinician bears down slightly on the needle 504 to apply negative pressure to the needle 504, which causes the needle to bend slightly and create broken fibers or pockets 422. The needle 504 is used to inject, retrograde threading the complete distance of the area designated. In other words and as shown in the results of FIG. 4B, the broken fibers or pockets are replaced with product 424 which provides lift to smooth out the skin. A series of lateral passes can be made to provide supportive columns.

After having completed the supportive columns (i.e., created by the product filled pockets), the user should resist the urge to massage them. It should be noted that the product filled pockets are supportive rods. Placed in an arc shape, if they are smashed, they will end up as non-cylindrical and unsupportive.

If the user failed to "stop short," they may see small nodules at some of the injection points. Should this occur, it may be desirable to press on the bumps with a cotton-tipped applicator to soften them.

The amount of support columns needed can be determined by using a cotton tip applicator to lift the skin to see if a correction can be made. The shadow of the folds can be followed until the correction is optimal.

The volume of filler injected during each pass will vary in amount, depending on the length of the needle and amount of correction needed. As a non-limiting example, a general rule of thumb is 0.1 cubic centimeter (cc) or milliliter (ml) for a short needle and 0.15 cc for a longer needle. Each column should be about 1-2 centimeters apart, or wherever needed for optimal correction.

The described procedure speaks specifically to the Nasolabial folds. However, the principles apply to any area of the face or body that is in need of lifting and redirecting upward. Once the patient has been injected in one or all the areas in need of volume reassignment, they have been provided a dermal lift according to the present invention.

(3) Conclusion

The present invention is a method for injecting fillers into the dermis of a patient using an arcing technique that arcs a needle to dissect collagen fibers, which creates a pocket for volume. The fillers referenced to are any dermal filler or "volumizer." When the fibroblasts are intentionally stretched, as exaggerated with the arcing technique, the mechanical stretching stimulates the fibroblasts to synthesize type 1 collagen. The outcome of this "tissue engineering" is an increase in neocollagenesis, resulting in an increase in clinical persistence (or longevity) of the dermal fillers, when compared to traditional methods of filling. The fillers are then placed into the dermis using two crucial components: (1) Using three dimensions of the skin; and (2) Using vectors to strategically work as scaffolding for the lax tissue. Thus, the "threads" of dermal fillers are placed strategically in vectors as a vehicle to pull the patient's own lax tissue into the patient's areas of hollows.

What is claimed is:

1. A method for injecting fillers into the dermis, comprising acts of:
    injecting a needle of a syringe filled with a filler into a patient's facial dermis at an insertion point;
    applying pressure to the needle to cause it to arc within the dermis and create pockets in the dermis;
    releasing the filler into the dermis while simultaneously applying pressure to the needle and withdrawing the needle from the patient's dermis, thereby positioning a filler within the patient's dermis to raise a facial depression.

2. The method as set forth in claim 1, wherein the insertion point is approximately one centimeter lateral and one centimeter superior to a fold that is associated with the facial depression.

3. The method as set forth in claim 2, wherein the needle is injected into the dermis until it is approximately one half a centimeter past the fold.

4. The method as set forth in claim 3, wherein in releasing filler into the dermis, pressure is applied to the needle and the needle is withdrawn such that as the needle exits the patient, the needle is at an angle with respect to the patient in a range of 60 to 75 degrees.

5. The method as set forth in claim 4, wherein in applying pressure to the needle to cause it to arc within the dermis and create pockets in the dermis, the dermis includes fibroblasts which are intentionally stretched through creating pockets in the dermis, thereby stimulating the fibroblasts to synthesize type 1 collagen and support the facial depression.

* * * * *